(12) United States Patent
Martin

(10) Patent No.: US 7,377,933 B2
(45) Date of Patent: May 27, 2008

(54) SURGICAL INSTRUMENT

(75) Inventor: Eugen Martin, Rietheim-Weilheim (DE)

(73) Assignee: S.U.A. Martin GmbH & Co. KG, Rietheim-Weilheim (DE)

( * ) Notice: Subject to any disclaimer, the term of this patent is extended or adjusted under 35 U.S.C. 154(b) by 737 days.

(21) Appl. No.: 10/998,514

(22) Filed: Nov. 29, 2004

(65) Prior Publication Data

US 2006/0116706 A1 Jun. 1, 2006

(51) Int. Cl.
*A61B 17/00* (2006.01)
(52) U.S. Cl. .............. 606/206; 606/205; 606/208; 83/318; 83/319; 83/320
(58) Field of Classification Search ............ 606/208, 606/205; 83/318–324
See application file for complete search history.

(56) References Cited

U.S. PATENT DOCUMENTS

| | | | | |
|---|---|---|---|---|
| 5,342,391 A | * | 8/1994 | Foshee et al. | 606/205 |
| 5,483,952 A | * | 1/1996 | Aranyi | 600/131 |
| 5,584,844 A | | 12/1996 | Weisshaupt | |
| 5,626,608 A | * | 5/1997 | Cuny et al. | 606/205 |
| 5,735,874 A | * | 4/1998 | Measamer et al. | 606/208 |
| 5,746,759 A | * | 5/1998 | Meade et al. | 606/170 |
| 5,827,323 A | * | 10/1998 | Klieman et al. | 606/205 |
| 5,961,531 A | * | 10/1999 | Weber et al. | 606/167 |
| 6,117,158 A | * | 9/2000 | Measamer et al. | 606/208 |
| 6,126,674 A | * | 10/2000 | Janzen | 606/206 |
| 6,506,208 B2 | * | 1/2003 | Hunt et al. | 606/205 |
| 6,520,979 B1 | | 2/2003 | Loubens | |
| 6,699,254 B1 | * | 3/2004 | Tontarra | 606/83 |
| 6,802,852 B2 | | 10/2004 | Tontarra | |
| 2003/0088268 A1 | | 5/2003 | Weinmann | |
| 2003/0216740 A1 | | 11/2003 | Michelson | |
| 2004/0073232 A1 | * | 4/2004 | Widmann | 606/139 |
| 2004/0254605 A1 | * | 12/2004 | DiFrancesco et al. | 606/205 |

* cited by examiner

*Primary Examiner*—Terrell McKinnon
*Assistant Examiner*—Erin Colello
(74) *Attorney, Agent, or Firm*—Akerman Senterfitt; Stephan A. Pendorf; Peter A. Chiabotti

(57) ABSTRACT

Surgical instrument which has a main part (10) with a shaft (12) and a fixed handle part (14), on which a moveable handle part (20) is supported pivotably. The pivotable handle part (20) engages through a slit (18) of the main part (10) and is linked to a slider (16). The slider (16) is guided axially shifted on the shaft (12) so that it cannot be removed. At the proximal end of the work stroke the slider (16) can be removed from the guide and shaft. Spring tongue (50) arranged on the pivotable handle part (20) comes against the main part (10) when the handle parts (14, 20) are spread apart and prevents the slider (16) from entering the cleaning position in which it is released from the shaft (12). The spring tongue (50) can be pressed against the moveable handle part (20) in order to enter the slit (18) of the main part and to release the locking.

7 Claims, 6 Drawing Sheets

SURGICAL INSTRUMENT

FIELD OF THE INVENTION

The invention concerns a surgical instrument with a main part, on which a shaft is formed distally, with a slider, which is guided so that it can move on the shaft, and with a handle which has a fixed handle part, formed on the main part, and a moveable part. The moveable handle part penetrates into a slit of the main part and it is supported in this slit so that it can be pivoted around a rotary axis with respect to the fixed handle part and is linked to the proximal end of the slider. The slider is guided inseparably on the shaft in the region of a distal front working stroke and becomes free from guided connection with the shaft in a cleaning position which is proximally behind the working stroke, and then can be separated from the shaft. The fixed handle part and the moveable handle part are spread apart by spring force in order to pull the slider back on the shaft and can be pressed together against the spring force in order to shift the slider forward on the shaft for the operation of the instrument.

BACKGROUND OF THE INVENTION

Such surgical instruments are used for various surgical interventions, in which case contact parts designed according to the purpose of application are formed on the distal end of the shaft and on the distal end of the slider. These contact parts can be, for example, parts of a punch, for removing tissue, bones, and cartilage from the human body. By spreading apart the handle parts, the contact parts are separated from one another in the axial direction, so that the instrument is open for the intervention. By pressing the handle parts together against the spring force, the contact parts are made to contact in order to separate the tissue or similar lying between them.

The shaft and slider lie against each other with sliding surfaces and are engaged with each other with guides. After use in surgery, the surgical instruments must be cleaned and sterilized in order to avoid transmission of infections, diseases or similar in subsequent interventions. In addition, this cleaning also helps in maintaining the function and quality of the instrument. In order to be able to thoroughly clean and sterilize the sliding surfaces and guides, it is necessary to be able to separate the slider from the shaft. For this purpose, the slider is moved in the proximal direction into the cleaning position, in which the guides are disengaged so that the slider and shaft can be lifted up and separated. In order that the slider cannot be moved unintentionally into the cleaning position during the use of the instrument and thus become separated from the shaft, a locking member is provided which, in a locking position, prevents movement of the slider beyond the proximal end of its working stroke, into the cleaning position. The locking member can be moved from the locking position into a release position in which the locking member permits movement of the slider into its cleaning position.

DESCRIPTION OF THE RELATED ART

U.S. Pat. No. 6,126,674 shows such a surgical instrument in which a locking part is arranged on the fixed handle part between the locking position and the release position, in a rotatable manner. US 2004/0073232 A1 shows such a surgical instrument in which a locking part is arranged between the locking position and the release position so that it can slide on the main part. U.S. Pat. No. 6,699,254 B1 shows such a surgical instrument in which a locking part is arranged between the locking position and the release position so it can be pivoted on the fixed handle part. In these cases, the locking part in the locking position blocks the shifting path of the slider and in the release position it is removed from this shifting path.

Moreover, U.S. Pat. No. 6,699,254 B1 shows an instrument in FIG. 5 in which a locking part is designed as a lever which is applied to the fixed handle part and goes through the moveable handle part. In the locked position, the lever prevents the spreading apart of the handle parts beyond the proximal end of the working stroke and it can be pivoted into a release position, in which it releases the moveable handle part for further spreading apart.

In US 2003/0088268 A1 a locking part is arranged on the moveable handle part and comes in contact with the main part in the locking position, as a result of which the spreading apart of the handle parts is limited when the slider reaches the proximal end of the working stroke. The locking part can be rotated from its locking position into a release position, in which the locking part does not impede further spreading apart of the handle parts so that the slider can be moved beyond the proximal end of the working stroke into the cleaning position.

In these surgical instruments of the art, the locking part consists of several individual parts which are mounted on the instrument so they can move. First of all, this means a considerable expenditure with regard to the construction and mounting of it. On the other hand, these locking parts with complicated structure themselves present a problem with regards to cleaning and sterilization. Finally, the locking parts are in the region of the handle which is held by the hand of the surgeon so that the locking parts may have an adverse influence on the handling of the instrument.

SUMMARY OF THE INVENTION

Therefore, the task of the invention is to improve a surgical instrument of the type described at the outset, with simple construction of the locking part, which permits good cleaning and sterilization and does not have an adverse influence on the shape and handling of the handle.

According to the invention, this task is solved by the fact that the locking part is a spring tongue which is applied with one of its ends onto the distal front side of the moveable handle part and is directed with its other free end toward the main part, that the free end of the spring tongue is spread away in the locked position from the moveable handle part with spring force, as a result of which, when the handle parts are spread apart, it contacts the main part and limits the spreading movement of the moveable handle part and that the free end of the spring tongue can be pressed against its spring force into its release position on the moveable handle part, as a result of which the free end can enter into the slit of the main part that holds the moveable handle part and then further spreading apart of the moveable handle part is not hindered.

Preferably, the spring tongue is arranged on the moveable handle part in such a way that, in the spread-apart locked position, the distal contour of the spring tongue matches the distal contour of the moveable handle part. Behind the spring tongue, the moveable handle part has a recess into which the spring tongue can be pressed in the release position. In this embodiment, in the entire handle of the instrument, the contour of the areas that come into contact with the hand of the surgeon are unchanged by the locking part, so that the surgeon can hold and handle the instrument in the accustomed manner.

In an advantageous embodiment, the region of the main part, which is contacted by the free end of the spring tongue in the locked position, is separated from the slit of the main part by a barrier. As a result of this, pressing the spring tongue during the use of the instrument unintentionally into the release position, in which the spring tongue enters into the slit, is prevented.

The linked joint between the proximal end of the slider and the moveable handle part can be designed in such a way that, although this joint permits pivoting of the slider away from the shaft, the shaft is held inseparably on the pivotable handle part and thus on the instrument. This has the advantage that the slider is held on the instrument even during cleaning and sterilization, so that for subsequent assembly of the instrument the slider is always arranged unchangeably on the instrument. In another embodiment, the linked joint between the proximal end of the slider and the moveable handle part can also be designed so that it is separable and thus the slider can be separated completely from the rest of the instrument for cleaning and maintenance.

BRIEF DESCRIPTION OF THE DRAWINGS

The invention will be explained in more detail below with the aid of a practical example shown in the drawing. The following are shown.

DETAILED DESCRIPTION OF THE INVENTION

Figure 1:
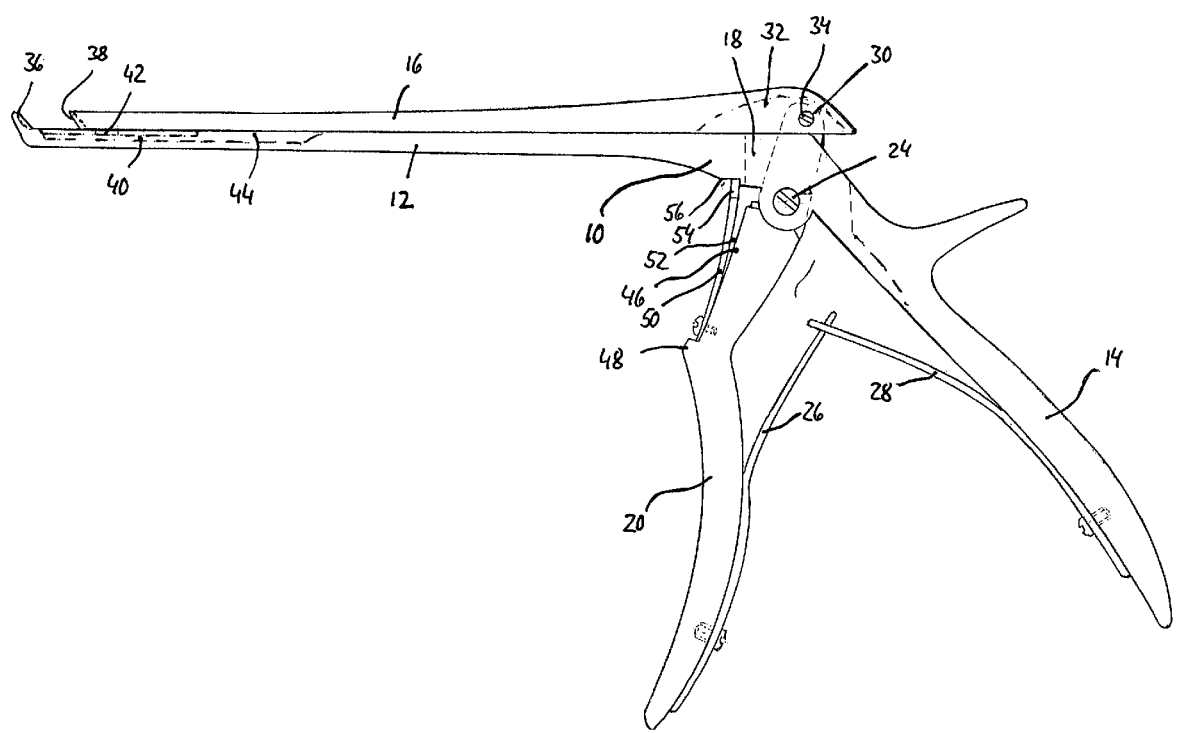
FIG. 1 is a side view of the instrument in the open use position.
Figure 2:
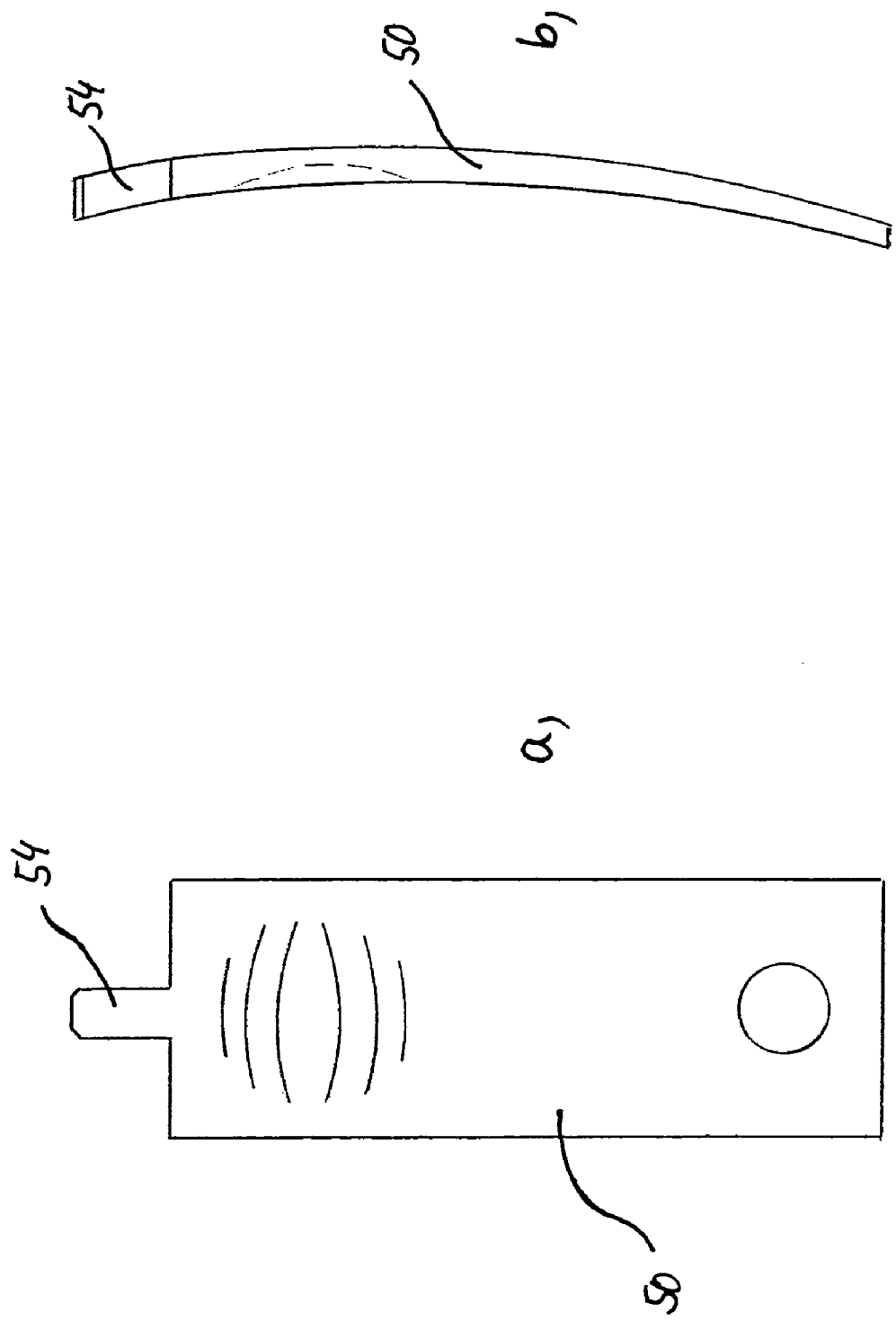
FIG. 2 shows the locking part of the instrument in a) front view and b) side view.

In the practical example shown in the drawing the surgical instrument is formed as a punch, which is used for example, for removing parts of tissue, bone or cartilage surgically.

The instrument which is made completely of metal, preferably of steel, has a main part 10 which is one piece at the distal end with a shaft 12. Furthermore, a fixed handle part 14 is formed proximally on the main part 10 and the handle part is at an angle to shaft 12. A slider 16 is arranged on the flat top side of shaft 12 and can be moved against shaft 12 axially. A through-slit 18 is milled in the main part 10 in its axial middle plane. A moveable handle part 20 goes through slit 18 and is supported in main part 10 pivotably. For this purpose, the handle part 20 is attached pivotably on a rotary axis 22 which goes through slit 18 perpendicularly, and the handle part is attached to main part 10 with the aid of a carriage bolt 24. In this way, the moveable handle part 20 can be pivoted against the rigid handle part 14. Leaf springs 26 and 28 are inserted between the fixed handle part 14 and the moveable handle part 20 and these springs hold the handle parts 14 and 20 spread apart. An end 30 of the moveable handle part 20 which is extended beyond rotary axis 22 engages into a recess 32 which is formed in the bottom side of slider 16, on its proximal end. The end 30 of the moveable handle part is link-joined to slider 16 through a pin 34 which goes through the slider 16 and the end 30 in the region of the recess 32. In the practical example shown, the pin 34 is designed as a screw placed in a fixed manner fixed in slider 16 so that slider 16 and the moveable handle part 20, although they are linked pivotably together, cannot be separated from one another. Alternatively, the pin 34 can also be designed, for example, as a thumb screw so that it can be simply screwed out from slider 16, as a result of which the slider 16 and the moveable handle part 20 can be separated from one another. Contact parts 36 and 38 are arranged at the distal front end of shaft 12 and of slider 16; these become engaged when slider 16 is shifted distally forward. In the practical example shown, the contact parts 36 and 38 are designed as cheeks of a punch that become engaged. For other purposes of application of the instrument, the contact parts 36 and 38 can have another form which corresponds to the other purpose of application of the instrument.

In order to guide slider 16 on the shaft 12 so that it is axially moveable, a guide groove 40 is worked into the plane upper surface of shaft 12. The guide groove 40 runs in the axial direction in the distal front end of shaft 12 and has a cross-section which is broadened at the base of the groove, especially a T-shaped cross-section. Correspondingly, on the bottom side of slider 16, which lies against shaft 12, a guide bar 42 is formed. The guide bar 42 also runs in the axial direction in the distal front region of slider 16 and has a cross-section which corresponds to the cross-section of the guide groove 40. The guide bar 42 engages in the guide groove 40, whereby the axial design of the guide groove 40 and of guide bar 42 permits axially-guided shifting of slider 16 on shaft 12. The cross-sectional shape of the guide groove 40 and of the guide bar 42 ensures that the guide bar 42 is held with positive locking in guide groove 40 and that the slider 16 cannot be lifted out from shaft 12. The guide groove 40 has a widened section 44 at its proximal end, the width of which is greater than the maximum width of guide bar 42 and the axial length of which is longer than the axial length of guide bar 42. When the slider 16 is moved along shaft 12 in the proximal direction into a cleaning position in the back, in which the guide bar 42 coincides with the widened section 44 of the guide groove 40, then the guide bar 42 can be lifted out from the guide groove 40 in this widened section 44 or can be inserted there so that the slider 16 can be lifted from shaft 12 or can be placed onto shaft 12.

The moveable handle part 20 has on its distal front end a contour which is adapted to the hand of the surgeon ergonomically so that the hand of the surgeon holding the instrument lies with the second finger against an upper region 46 which is separated from a lower region by raised part 48 protruding in the distal direction, the middle finger and the ring finger of the hand lying against the lower region. In the upper region 46 of the moveable handle part 20, a locking member is arranged which is designed as a spring tongue 50. The spring tongue 50 has a width which corresponds to the width of handle part 20. The spring tongue 50 is arranged at the front side of handle part 20 with its lower end in the region of raised part 48. From the raised part 48, the spring tongue 50 extends upward in front of the upper region 46 of handle part 20 upward and is directed with its free end against the lower side of main part 10. The free end of spring tongue 50 is thus spread apart from the front side of handle part 20 in the distal direction, so that a milled-in gap 52 remains free between the spring tongue 50 and the distal front side of the upper region 46 of handle part 20. At the free end of spring tongue 50, the width of the spring tongue 50 is reduced to a narrower engaging tip, the width of which is somewhat smaller than the width of slit 18 of main part 10. Due to this arrangement, the spring tongue 50 fits into the distal contour of the moveable handle part 20 so that the spring tongue 50 does not alter the previously described distal contour of the moveable handle part 20 in comparison to a conventional handle part. The shape of the handle of the instrument thus practically does not differ at all from the shape of a grip of a conventional instrument, so that the surgeon can handle the instrument in the manner accustomed to with the conventional instruments.

Figure 5:
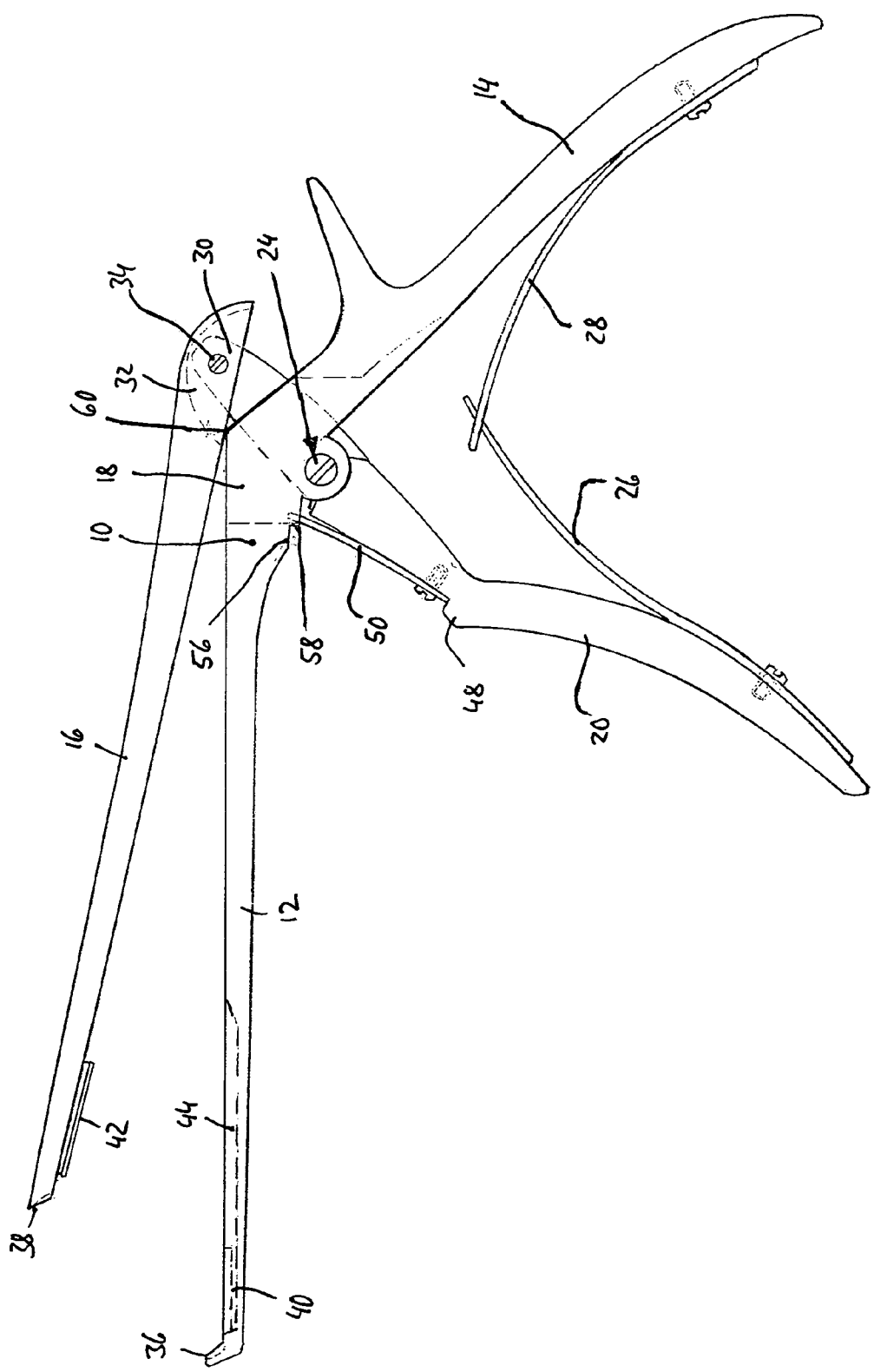
FIG. 5 is a side view of the instrument in the disassembled state and FIG. 6 is a corresponding partial axial section of the instrument according to FIG. 3 in the disassembled position of FIG. 5.
Figure 6:
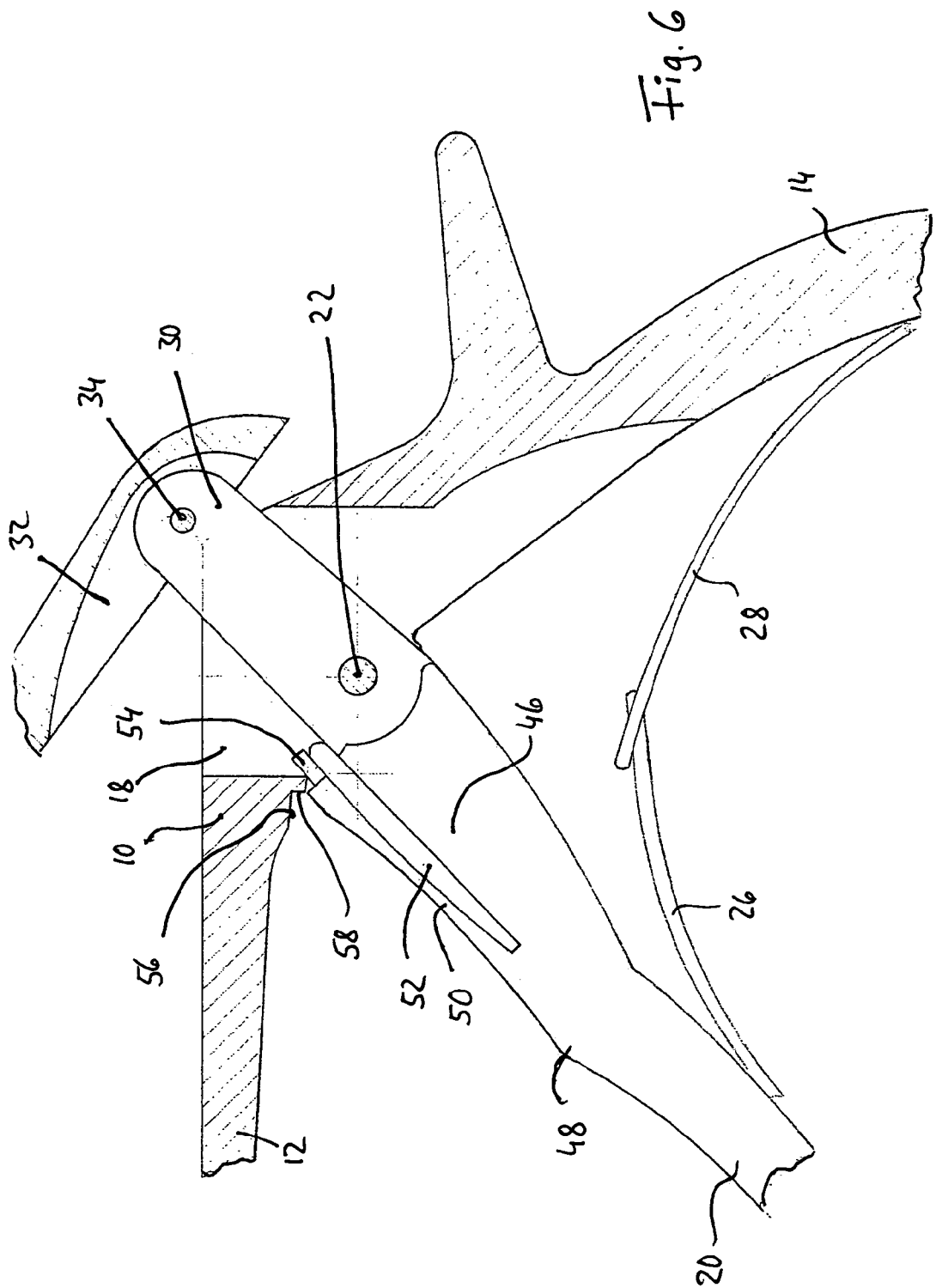

The spring tongue 50 consists of a metal with elastic springiness, and can be made, for example, from the same stainless material of which the rest of the instrument is made. In the practical example shown in FIGS. 1, 2, 4 and 5, the spring tongue 50 is screwed at its lower end into the region of the raised part 48 onto the distal front end of the moveable handle part 20. However, instead of fastening with a screw, other known types of fastening are also possible. For example, the spring tongue can be secured by laser welding, hard soldering or welding in a protective gas onto handle part 20. It is also possible to make the spring tongue 50 in one piece with the moveable handle part 20, and in this case, in order to produce the spring tongue 50 the gap 52 is milled out from the full material of handle part 20. Such embodiments are shown in FIGS. 3 and 6.

Figure 3:
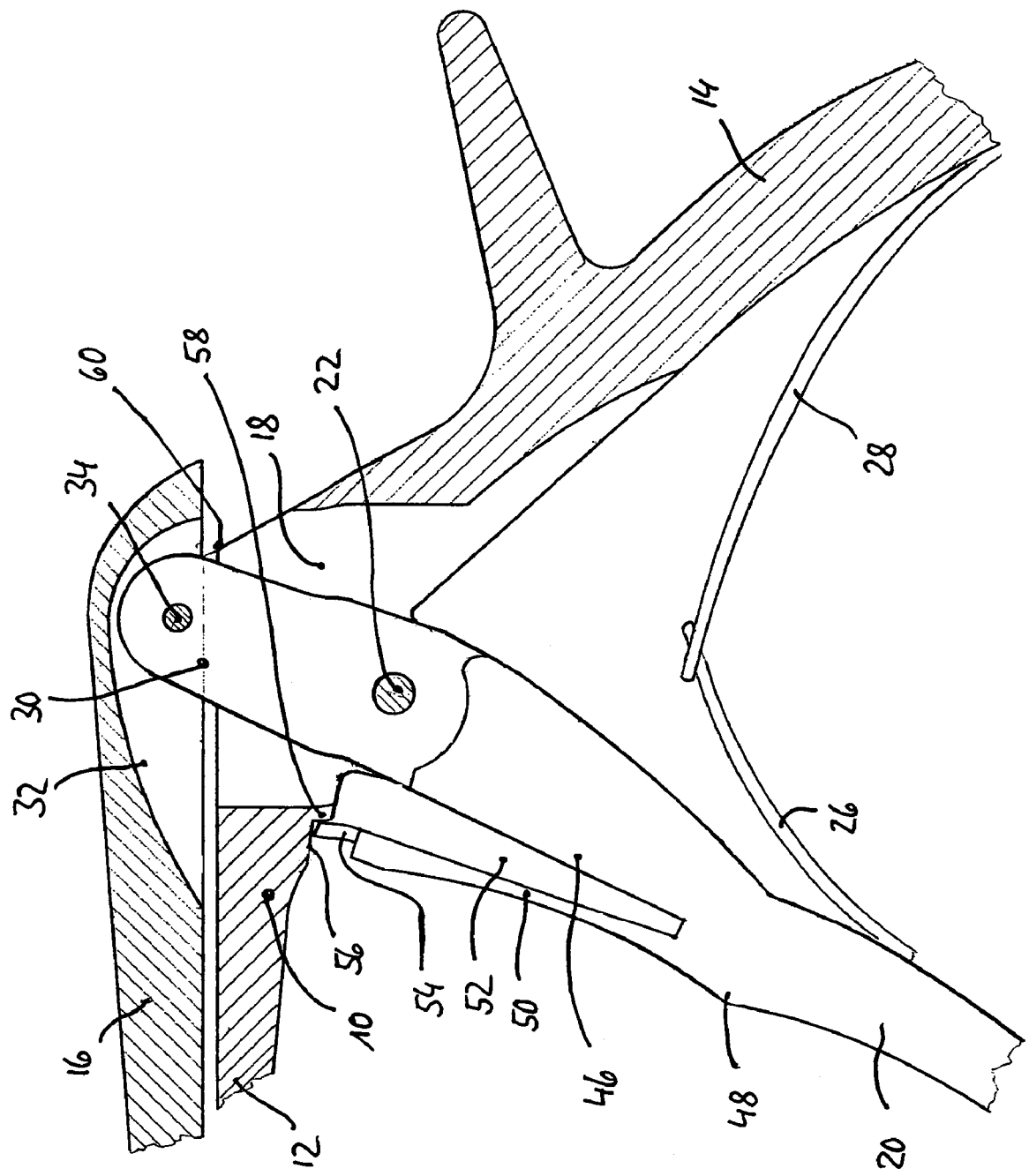
FIG. 3 is a partial longitudinal section through the instrument in the position of FIG. 1, with a modified locking part.

The mode of functioning of the instrument will be described below:

During the use of the instrument, it is in the open use position shown in FIGS. 1 and 3. In this open use position, the leaf springs 26 and 28 spread the handle parts 14 and 20 apart, as a result of which the moveable handle part 20 with its upper end 30 pulls the slider 16 backward on the shaft 12 in the proximal direction all the way back to the end of the working stroke. The contact parts 36 and 38 are separated from one another and opened. The guide bar 42 still engages in the guide groove 40 so that the slider 16 is held on shaft 12.

The spreading movement of the moveable handle part 20 by the leaf springs 26 and 28 is limited at the end of the work stroke by the fact that the spring tongue 50 contacts, with its free end and the engaging tip formed on it, the bottom side of main part 10, as it can be seen in FIGS. 1 and 3. In the region in which the engaging tip 54 contacts spring tongue 50, a flat milled out part 56 is provided on the bottom side of main part 10, which is separated from the milled out slit 18 of main part 10 by a stepped barrier 58. The engaging tip 54 lies against the milled out part 56 under the action of leaf springs 26 and 28 and the barrier 58 reliably prevents unintended introduction of the engaging tip 54 into slit 18.

Figure 4:
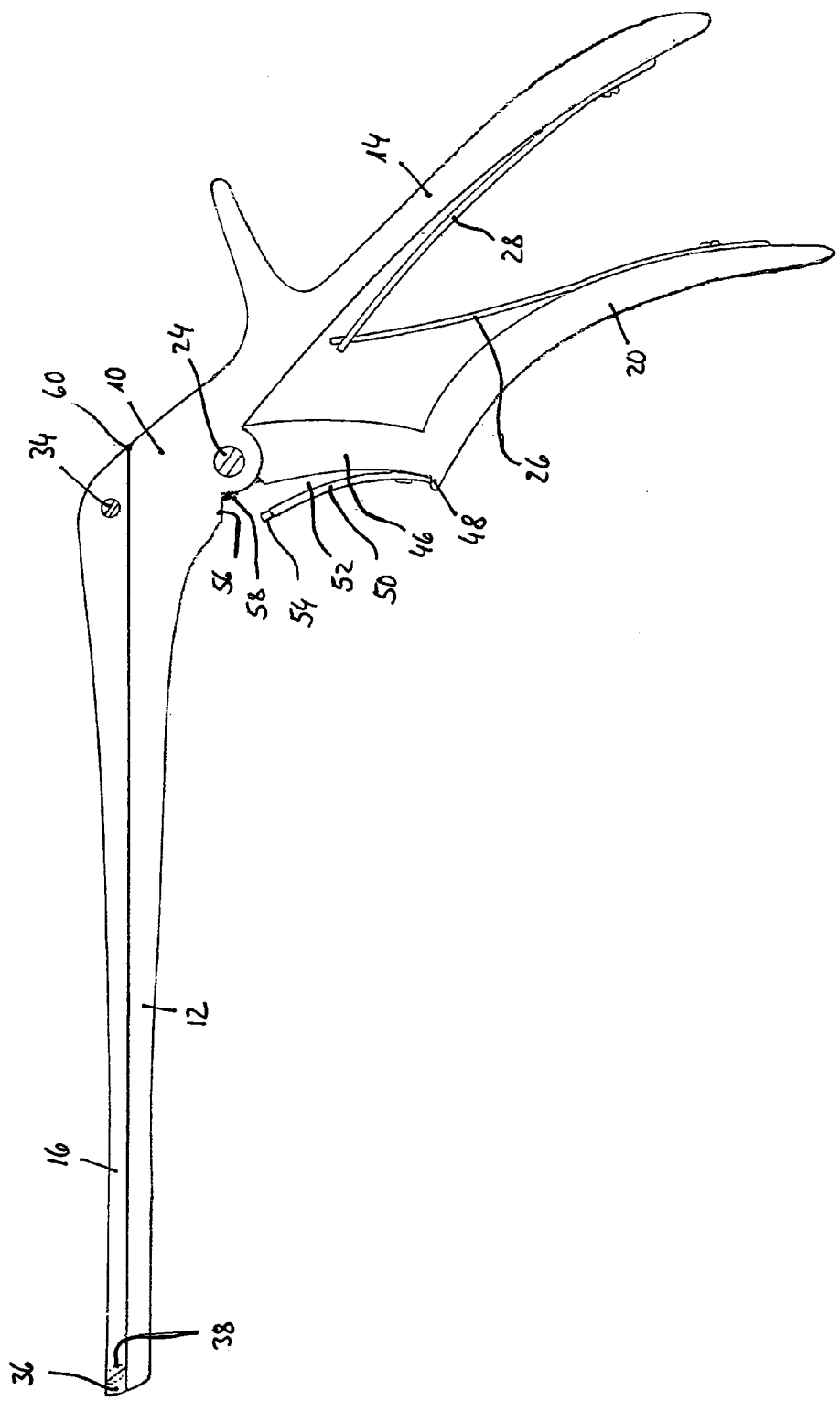
FIG. 4 is a side view of the instrument in the closed use position.

During the use of the instrument, the surgeon holds handle parts 14 and 20 with his or her hand and presses the moveable handle part 20 against the force of leaf springs 26 and 28 against the fixed handle part 14. As a result of the pivoting movement of the moveable handle part 20, the slider 16 is pushed distally forward on the shaft, so that the contact parts 36 and 38 become engaged as shown in FIG. 4. As a result of this, for example, with the contact parts 36 and 38 which are designed as a punch, a part of a tissue, a bone or cartilage can be separated. In this working stroke of the slider, from the open use position shown in FIG. 1 into the closed use position shown in FIG. 4, the slider 16 is guided axially on shaft 12 by the guide bar 42 engaged in guide groove 40 and is held so that it cannot be removed from the shaft 12.

If during this working stroke while using the instrument, the moveable handle part 20 is pivoted against the fixed handle part 14, then the free end of the spring tongue 50 is lifted up from the main part 10, as shown in FIG. 4. If the handle is released again, then the leaf springs 26 and 28 move the moveable handle part 20 again away from the fixed handle part 14, as a result of which spring tongue 50 again comes into contact with the milled out part 56 with its engaging tip 54. Since the free end of spring tongue 50 is spread apart by the elastic spring force of spring tongue 50 away from handle part 20, the engaging tip 54 reliably lies against milled out part 56 in front of barrier 58. The spreading apart of handle parts 14 and 20 and the movement of slider 16 are reliably limited in this way before the guide bar 42 from guide groove 40 would arrive in the proximal direction beyond the working stroke into the widened section 44.

If the instrument is to be cleaned and sterilized, then first the moveable handle part 20 is pivoted against the force of leaf springs 26 and 28 with respect to the fixed handle part 14, until the engaging tip 54 of the spring tongue 50 is lifted up at least above the height of barrier 58 from milled out part 56. Then the free end of spring tongue 50 is pressed, against its elastic spring force, against the distal front side of handle part 20, so that the free end with the engaging tip 54 is pressed into gap 52 and lies against handle part 20. Now the moveable handle part 20 is released so that it is pivoted by leaf springs 26 and 28 again away from the fixed handle part 14, whereby the free end of spring tongue 50 is pressed against handle part 20. In this pivoting movement of the moveable handle part 20, now the engaging tip 54 of spring tongue 50 arrives directly in front of the moveable handle part 20 into slit 18 of main part 10, as shown in FIGS. 5 and 6. Since the engaging tip 54 can now enter into slit 18, the pivoting movement of the moveable handle part 20 is no longer limited. Handle part 20 can be spread away from fixed handle part 14 further by leaf springs 26 and 28, as a result of which the moveable handle part 20 with its end 30 pulls the slider 16 further in the proximal direction beyond the end of the working stroke toward the back and the guide bar 42 enters the widened section 44 of guide groove 40. In this cleaning position now the guide bar 42 can be removed from the widened section 44 and thus the slider 16 can be removed from shaft 12, as shown in FIG. 5. During the pivoting movement of the moveable handle part 20, pin 34, which joins slider 16 with end 30 of handle part 20, moves on a circular arc. As shown in FIG. 5, as a result of this, the proximal end of slider 16 is pulled over a proximal back end edge 60 of the top side of shaft 12, as a result of which the distal end of the slider 16 is pivoted upward and is taken off from shaft 12. The sliding surfaces of shaft 12 and of slider 16 and the guide groove 40 and guide bar 42 thus become free and are accessible to thorough cleaning and sterilization.

If the instrument is to be used again, then merely the distal end of slider 16 is to be pressed from the cleaning position shown in FIG. 5 against shaft 12 so that the guide bar 42 lies again in the widened section 44 of guide groove 40. Then the handle parts 14 and 20 are pressed together against the force of leaf springs 26 and 28, as a result of which slider 16 is pushed forward in the distal direction and the guide bar 42 will enter guide groove 40 axially. In this pivoting of the moveable handle part 20, the engaging tip 54 is lifted out from slit 18 of main part 10. As soon as the engaging tip 54 left slit 18, the spring force of spring tongue 50 spreads the free end of handle part 20 away so that the engaging tip 54 comes again in front of barrier 58. When the handle is released, spring tongue 50 now lies against the milled out part 56 again and locks the shifting of slider 16 in the proximal direction.

Reference List

| 10 | Main part |
| 12 | Shaft |
| 14 | Fixed handle part |
| 16 | Slider |
| 18 | Slit |
| 20 | Moveable handle part |
| 22 | Rotary axis |
| 24 | Carriage bolt |
| 26 | Leaf spring |
| 28 | Leaf spring |
| 30 | End of 20 |
| 32 | Recess |
| 34 | Pin |
| 36 | Contact part |
| 38 | Contact part |
| 40 | Guide groove |
| 42 | Guide bar |
| 44 | Widened section |
| 46 | Upper region |
| 48 | Raised part |
| 50 | Spring tongue |
| 52 | Gap |
| 54 | Engaging tip |
| 56 | Milled out part |
| 58 | Barrier |
| 60 | End edge |

The invention claimed is:

1. A surgical instrument with
a main part (10) on which a shaft (12) is formed distally,
a slider (16), which is guided axially moveably on the shaft (12), and
a handle, which has a fixed handle part (14) and a moveable handle part (20) formed on the main part (10),
wherein the moveable handle part (20) engages in a slit (18) of the main part (10), is pivotably supported in this slit (18) around a rotary axis (22) with respect to the fixed part (14) and is linked to the proximal end of the slider (16),
wherein the slider (16) is guided in the region of a distal front working stroke on the shaft (12) so that it cannot be removed and then is released from the guided connection with the shaft (12) in a proximal cleaning position lying beyond the working stroke and can be separated from the shaft (12),
wherein the fixed handle part (14) and the moveable handle part (20) are moveable between an apart and a together position so as to be biased apart by a spring force (26, 28) in order to pull back the slider (16) on the shaft (12) and so as to be pushed together against spring force in order to move the slider (16) on the shaft (12) in order to operate the instrument,
wherein a locking part is arranged on the moveable handle part (20) which, in the locking position, contacts the main part (10) and limits the spreading apart of handle parts (14, 20) when the slider (16) reaches the proximal end of the working stroke,
wherein the locking part can be moved from its locking position into a release position in which the locking part does not limit the spreading apart of the handle parts (14, 20), so that the slider (16) can be moved beyond the proximal end of the working stroke into its cleaning position, and
wherein the locking part is a spring tongue (50) which is brought with its one end to the distal front edge of the moveable handle part (20) and is directed with its free other end against the main part (10),
wherein the free end of the spring tongue (50) is spread apart from the handle part (20) under spring force in the locked position of the moveable handle part (20), as a result of which it arrives against the main part (10) when the handle parts (14, 20) are spread apart and limits the spreading movement of the moveable handle part (20) and
wherein the free end of the spring tongue (50) can be pressed onto the moveable handle part (20) against its spring force in the release position, as a result of which the free end of the spring tongue (50) enters from a position outside the slit (18) can enter into the slit (18) of the main part (10) which holds the moveable handle part (20) and then no longer hinders further spreading movement of the moveable handle part (20).

2. The surgical instrument according to claim 1, wherein the spring tongue (50) is screwed on, welded on or soldered on the moveable handle part (20) or is milled out from the handle part (20).

3. The surgical instrument according to claim 1, wherein the spring tongue (50) fits in the distal contour of the moveable handle part (20).

4. The surgical instrument according to claim 3, wherein the width of the spring tongue (50) essentially corresponds to the width of the moveable handle part (20) and wherein the width of the spring tongue (50) on its free end is reduced to an engaging tip (54), the width of which is smaller than the width of the slit (18) of the main part (10).

5. The surgical instrument according to claim 1, wherein the free end of the spring tongue (50) is supported on a deeper milled out part (56) of the main part (10) in the locked position, being separated from the slit (18) with a stepped barrier (58).

6. The surgical instrument according to claim 1, wherein the slider (16) and the shaft (12) are guided on their distal end through a guide bar (42) and a guide groove (40), which engage into one another with positive locking, and that the guide groove (40) has a widened section (44) proximally, which serves for inserting and removing the guide bar (42) in the cleaning position.

7. The surgical instrument according to claim 1, wherein the slider (16) and the moveable handle part (20) are connected together so that they can be separated or not separated.

* * * * *